United States Patent
Srinivas et al.

(10) Patent No.: US 7,365,214 B2
(45) Date of Patent: Apr. 29, 2008

(54) PROCESS FOR THE PREPARATION OF CYCLIC CARBONATES

(75) Inventors: Darbha Srinivas, Maharashtra (IN); Rajendra Srivastava, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 628 days.

(21) Appl. No.: 10/671,869

(22) Filed: Sep. 29, 2003

(65) Prior Publication Data

US 2005/0070724 A1    Mar. 31, 2005

(51) Int. Cl.
*C07D 321/00*    (2006.01)
*C07D 317/08*    (2006.01)

(52) U.S. Cl. .................. 549/228; 549/229; 502/124

(58) Field of Classification Search ............. 549/229, 549/228; 502/124

See application file for complete search history.

(56) References Cited

U.S. PATENT DOCUMENTS 6,407,264 B2 *    6/2002    Kim et al. .................. 549/229

OTHER PUBLICATIONS

Sabater t al. Chem. Commun., 1997, pp. 1285-1286.*

* cited by examiner

*Primary Examiner*—Joseph K. McKane
*Assistant Examiner*—Yong Chu
(74) *Attorney, Agent, or Firm*—Nixon & Vanderhye P.C.

(57) ABSTRACT

The present invention provides an improved process for the preparation of cyclic carbonates which comprises reacting an olefins or its epoxide with carbon dioxide or a mixture of oxygen-containing compound and carbon dioxide, in the presence of zeolite-based catalyst and a Lewis base co-catalyst, at a minimum pressure of 30 psig and temperature between 40 to 120° C. for 0.5 to 4 hrs., separating the catalyst and recovering the corresponding cyclic carbonate formed by conventional methods.

12 Claims, No Drawings

PROCESS FOR THE PREPARATION OF CYCLIC CARBONATES

FIELD OF THE INVENTION

The present invention relates to a process for the preparation of cyclic carbonates. More particularly, the present invention relates to an environmentally-friendly, non-toxic, phosgene-free, clean process for the preparation of cyclic carbonates, precursors of polycarbonates, through a reaction of olefins or their epoxides with carbon dioxide or a mixture of carbon dioxide and oxygen-containing compound, in the presence of a zeolite-based catalyst and a Lewis base co-catalyst.

BACKGROUND OF THE INVENTION

Cyclic carbonates are an important raw material for engineering plastics like polycarbonates. Currently, the latter are manufactured using phosgene, a highly toxic, irritating and corrosive gas, inhalation of which can cause fatal respiratory damage. The total demand of polycarbonates is more than 1.2 million tons per annum. The demand for polycarbonates is expected to increase by approximately 9% per year. Plastics of this material are widely used in electric and electronic industry, building industry, optical data storage media, automotive industry, package industry, headlamp diffuser lens and bottles for water and milk. Polycarbonates of aliphatic type are used as plasticizers, stabilizers for vinyl chloride polymers, co-monomers in polyurethane synthesis, lubricants, elastomers (functionalized PC with pendent vinyl group) and biodegradable and biomedical materials for drug delivery. Polycarbonates are commercially prepared by condensation of 4-hydroxydiphenylbutane and phosgene ($COCl_2$) in the presence of substituted amines and alkali (Encyclopedia of Chemical Processing and Design, Vol 40, Ed. by J. J. McKetta and W. A. Cunningham, Marcel Dekker Inc., New York, 1992, p. 136 and Ulmann's encyclopedia of Industrial Chemistry, Vol. A 21, Ed. by B. Elvers, S. Hawkins and G. Schulz, $5^{th}$ ed. VCH Verlagsgesellschaft, GmbH, Germany 1992, p. 207). However, this method of preparation is highly toxic and dangerous. Eco-friendly routes for the preparation of polycarbonates or their precursor cyclic carbonates are highly desirable.

Inoue et al. (J. Poly. Sci. Polym. Lett. Vol. 7, pp. 298 (1969)) reported for the first time that polycarbonates can be prepared by cyclo-addition of epoxides to carbon dioxide in the presence of zinc catalyst. However, this reaction usually requires high temperatures and pressures. Homogeneous catalysts like $CH_3SnBr_3$, $Ph_4SbBr$ and n-$Bu_3SnI$ were reported to be effective at low temperatures, but high concentration of the catalyst ($\geq 1$ mol %) is required (Matsuda et al., Chem. Lett. (1979) 573; Nomura et al., J. Org. Chem. 45 (1980) 3735; Baba et al., Bull. Chem. Soc. Jpn 60 (1987) 1552). This necessitates expensive catalyst separation and product purification. Organometallic complexes of Zn and the complexes of low-valent transition metals e.g., Ni(0) and Cu(I) were reported to exhibit higher catalytic activity but they are highly sensitive to air and moisture. Phthalocyanine and Schiff base complexes showed good activity for the cyclo-addition reaction (Ji et al., Appl. Catal. A: General 203 (2000) 329). Again, the catalyst separation is a major problem.

Exxon Research & Engineering Co. (U.S. Pat. No. 4,824, 969) has developed a process for preparing cyclic carbonate esters from olefins in a single reaction mixture using osmium compound, copper containing co-catalyst I (e.g., $CuBr_2$), co-catalyst II (e.g., pyridine) and water. Shell Oil Company (U.S. Pat. Nos. 4,826,887 and 4,826,953) reported the process for the preparation of polycarbonates in the presence of catalytic amounts of a double metal cyanine complex and (a) one or more salts composed of at least bivalent metal ions and metal-free anions having a solubility in water of at least 1 g/100 ml and one or more no-metal containing acids. U.S. Pat. No. 6,469,193 reports the preparation of aliphatic carbonates from aliphatic alcohols, alkyl halides and carbon dioxide in the presence of cesium carbonate and tetrabutyl ammonium iodide. U.S. Pat. No. 6,407,264 reports a process involving the reaction of alkylene oxide with carbon dioxide in the presence of a catalyst system comprising of a metal halide and pyridine or pyridine derivative. U.S. Pat Nos. 6,399,536, 5,391,767 and 6,288, 202 and UK Pat Appl. GB 2352449 A1, PCT Int. Appl. WO 2000008088 A1, Ger. Offen. DE 19737547 A1 and Eur. Pat. Appl. EP 864361 A2 are all related to this process. However, in all the prior art processes the reaction is in homogeneous medium, high catalyst amounts are needed which necessitates elaborate process as an additional step for catalyst separation/recycle. There are a few reports on the use of solid catalysts like silica supported guanidine (Barbarini et al Tetrahedron Lett. 44 (2003) 2931) and MCM-supported phthalocyanine (Lu et al., J. Mol. Catal. A: Chemical 186 (2002) 33) complexes for this reaction, however larger amounts catalyst and long reaction times (>15 h) are required for high yield of cyclic carbonate.

OBJECTS OF THE INVENTION

The main object of the invention is to provide an improved process for the preparation of cyclic carbonates having high conversion and high yields.

Another object is to provide a process for the production of cyclic carbonates wherein use of toxic phosgene is eliminated. Cyclic or polycarbonates are prepared by cyclo-addition of olefins or their epoxides to carbon dioxide in the presence of solid zeolite-based catalysts.

A further object of the invention is to prepare cyclic carbonates from olefins or their epoxides and carbon dioxide or mixture of oxygen-containing compound and carbon dioxide.

SUMMARY OF THE INVENTION

In the investigations leading to the present invention, it was found that when active centers or metal ions are isolated and substituted in the framework (for example in the in the case of metallosilicates) or encapsulated in the pores of zeolite, the activity is enhanced. Hence, the prior art catalysts i.e., neat complexes are not sufficiently active as the zeolite-based catalysts. These novel zeolite-based catalysts while retaining all the advantageous features of homogeneous catalysts like yields of the desired product etc., could be easily separated from the reaction products by simple filtration process, thereby not only avoids the tedious process of catalyst recovery characteristic of prior art processes, but also eliminates the presence of toxic elements like metal ions in the product and effluents. Hence the present invention is environmentally more beneficial. The present invention does not involve the toxic phosgene reactants and hence, unlike the commercial process it is safer.

Accordingly, the present invention provides an improved process for the preparation of cyclic carbonates which comprises reacting an olefin or an epoxide thereof with carbon dioxide or a mixture of oxygen-containing compound and carbon dioxide, in the presence of zeolite-based catalyst and a Lewis base co-catalyst, separating the catalyst and recovering the corresponding cyclic carbonate formed by conventional methods.

In one embodiment of the invention, the reaction is carried out at a minimum pressure of 30 psig and temperature in the range of 40 to 120° C. for 0.5 to 4 hrs.

In another embodiment of the invention the zeolite based catalyst is selected from the group consisting of a zeolite, a metallosilicate and a solid organometallic complex comprising of N and O-donor atoms encapsulated in a zeolite or zeolite-like material selected from an aluminosilicate, aluminophosphate and metallosilicate.

In another embodiment of the invention, the zeolite based catalyst is selected from an aluminosilicate of the molecular formula $M^{n+}_{x/n}[(AlO_2^-)_x(SiO_2)_y].z\,H_2O$ where n is valance of the charge corresponding cation m like sodium, potassium, cesium etc.; x assume value between 0 to 0.5, the ratio of x/y being less or equal to 1; or a zeolite containing an encapsulated organometallic complex having formula $(C_{32}H_{16}N_8M)$ wherein M=Al, Cu, Co or Ni.

In another embodiment of the invention, the metallosilicate has a composition
$(TiO_2)_x SiO_2$ where x=0 to 0.04.

In another embodiment of the invention, the organometallic complex consists of transition metal ions such as Al, Cu, Co and Ni and coordinated ligands containing N- and/or O-donor atoms such as phthalocyanines, porphyrins, Schiff bases, peraza macrocycles, pyridine or derivatives thereof.

In still another embodiment the olefin is of the formula $C_{(n)}H_{2(n)}$ wherein n=2 to 10 or its corresponding epoxide.

In still another embodiment the olefin or epoxide thereof is dissolved in a solvent selected from a polar and non-polar solvent.

In another embodiment of the invention, the solvent is selected from the group consisting of 1,2-dichloromethane, toluene, acetonitrile, methanol and water.

In yet another embodiment the Lewis base co-catalyst is selected from the group consisting of pyridine, a pyridine derivative, alkyl phosphene, aryl phosphene, alkyl ammonium salts and phosphonium salts.

In still another embodiment the oxygen-containing compound is selected from the group consisting of oxygen, air, nitrogen oxides, hydrogen peroxide and alkyl hydroperoxide.

In another embodiment the ratio of olefin/its epoxide to the catalyst is in the range of 2500:1 to 5:1

It is a feature of the process of the present invention that it is phosgene-free and more environmental-friendly.

It is yet another feature of the process of the present invention that the solid catalyst could be easily separated by simple filtration and could be reused with little loss in activity.

In still yet another feature, the conversions of the hydrocarbon or epoxide are greater than or equal to 85% and the selectivity for the carbonate is greater than or equal to 85%.

DETAILED DESCRIPTION OF THE INVENTION

The present invention is an environmental-friendly green process carried out in the presence of a zeolite-based catalyst at low temperatures and $CO_2$ pressures. The catalyst is easily separable by simple filtration and reused. Most importantly, the catalyst is highly efficient and only a small amount of it is needed. The method of the present invention utilizes a zeolite or metallosilicate or a solid organometallic complex comprising of N and O-donor atoms encapsulated in a zeolite or zeolite-like material such as aluminosilicate, aluminophosphate and metallosilicate or a like material having porous structure.

It is a surprising that the solid organometallic complex encapsulated in zeolite exhibits superior activity and high selectivity for the cyclic carbonate. The solid catalyst can be easily separated from the reaction mixture by simple filtration. Moreover, the reaction conditions like temperature and pressure are moderate and the process is atom-efficient. Molecular isolation and possible zeolite-metal interactions are the possible causes for the enhanced activity of the catalysts of present invention for this reaction.

In the investigations leading to the present invention, it was found that when active centers or metal ions are isolated and substituted in the framework (for example in the in the case of metallosilicates) or encapsulated in the pores of zeolite, the activity is enhanced. Hence, the prior art catalysts i.e., neat complexes are not sufficiently active as the zeolite-based catalysts. These novel zeolite-based catalysts while retaining all the advantageous features of homogeneous catalysts like yields of the desired product etc., could be easily separated from the reaction products by simple filtration process, thereby not only avoids the tedious process of catalyst recovery characteristic of prior art processes, but also eliminates the presence of toxic elements like metal ions in the product and effluents. Hence the present invention is environmentally more beneficial. The present invention does not involve the toxic phosgene reactants and hence, unlike the commercial process it is safer.

The present invention provides an improved process for the preparation of cyclic carbonates which comprises reacting an olefins or its epoxide with carbon dioxide or a mixture of oxygen-containing compound and carbon dioxide, in the presence of zeolite-based catalyst and a Lewis base co-catalyst, at a minimum pressure of 30 psig and temperature between 40 to 120° C. for 0.5 to 4 hrs., separating the catalyst and recovering the corresponding cyclic carbonate formed by conventional methods.

The solid catalyst may be a zeolite such as aluminosilicate having a molecular formula $M^{n+}_{x/n}[(AlO_2^-)_x(SiO_2)_y].z\,H_2O$ where n is the valance of the charge corresponding cation m like sodium, potassium, cesium etc.; x assume value between 0 to 0.5 the ration of x/y is less or equal to 1; or a zeolite containing an encapsulated organometallic complex having formula $(C_{32}H_{16}N_8M)$ where M=Al, Cu, Co or Ni. The metallosilicate preferably has a composition $(TiO_2)_x SiO_2$ where x=0 to 0.04.

The metal complex may consists of transition metal ions such as Al, Cu, Co and Ni and coordinated ligands containing N- and/or O-donor atoms such as phthalocyanines, porphyrins, Schiff bases, peraza macrocycles, pyridine or its derivatives.

The olefin may be of formula $C_{(n)}H_{2(n)}$ wherein n=2 to 10 or its corresponding epoxide. A solvent such as a polar or non-polar solvent exemplified by 1,2-dichloromethane, toluene, acetonitrile, methanol and water may be used to dissolve the olefin or its epoxide.

The Lewis base co-catalyst may be pyridine or pyridine derivatives, alkyl or aryl phosphene, alkyl ammonium salts and phosphonium salts. The oxygen-containing compound may be oxygen, air, nitrogen oxides, hydrogen peroxide and alkyl hydroperoxide. The ratio of olefin/its epoxide to the catalyst may be 2500:1 to 5:1. It is a feature of the process of the present invention that it is phosgene-free and more environmental-friendly. The solid catalyst could be easily separated by simple filtration and could be reused with little loss in activity.

In still yet another feature, the conversions of the hydrocarbon or epoxide are greater than or equal to 85% and the selectivity for the carbonate is greater than or equal to 85%.

This process of the present invention is described hereinbelow with reference to the examples which are illustrative only and should not be construed to limit the scope of the present invention in any manner.

EXAMPLE 1

This example illustrates the preparation of aluminium phthalocyanine encapsulated in zeolite-Y (AlPc-Y). Aluminium exchanged Y (Al—Y) was prepared first by ion exchanging zeolite NaY (5 g) with an aqueous solution of $Al_2(SO_4)_3.18H_2O$ (250 mg in 100 ml distilled water). In the preparation of zeolite-Y-encapsulated aluminium phthalocyanine, 3 gm of Al—Y was degassed for 8 h at 373 K in vacuum and then exposed to the vapors of 1,2-dicyanobenzene (10 g) at 533 K for 24 h. Nitrogen was used as a carrier gas. The solid was Soxhlet extracted with different solvents viz., acetone, pyridine, and acetonitrile. The sample AlPc-Y, thus obtained was finally dried at 373 K.

EXAMPLE 2

This example illustrates the preparation of copper phthalocyanine encapsulated in zeolite-Y (CuPc-Y). Copper exchanged Y (Cu—Y) was prepared first by ion exchanging zeolite NaY (5 g) with an aqueous solution of $Cu(NO_3)_2.2.5H_2O$ (250 mg in 100 ml distilled water). In the preparation of zeolite-Y-encapsulated copper phthalocyanine, 3 gm of Cu—Y was degassed for 8 h at 373 K in vacuum and then exposed to the vapors of 1,2-dicyanobenzene (10 g) at 533 K for 24 h. Nitrogen was used as a carrier gas. The solid was Soxhlet extracted with different solvents viz., acetone, pyridine, and acetonitrile. The sample CuPc-Y, thus obtained was finally dried at 373 K.

EXAMPLE 3

This example illustrates the preparation of cobalt phthalocyanine encapsulated in zeolite-Y (CoPc-Y). Cobalt exchanged Y (Co—Y) was prepared first by ion exchanging zeolite NaY (5 g) with an aqueous solution of $Co(CH_3COO)_2.4H_2O$ (250 mg in 100 ml distilled water). In the preparation of zeolite-Y-encapsulated cobalt phthalocyanine, 3 gm of Co—Y was degassed for 8 h at 373 K in vacuum and then exposed to the vapors of 1,2-dicyanobenzene (10 g) at 533 K for 24 h. Nitrogen was used as a carrier gas. The solid was Soxhlet extracted with different solvents viz., acetone, pyridine, and acetonitrile. The sample CoPc-Y, thus obtained was finally dried at 373 K.

EXAMPLE 4

This example illustrates the preparation of nickel phthalocyanine encapsulated in zeolite-Y (NiPc-Y). Nickel exchanged Y (Ni—Y) was prepared first by ion exchanging zeolite NaY (5 g) with an aqueous solution of $Ni(CH_3COO)_2.4H_2O$ (250 mg in 100 ml distilled water). In the preparation of zeolite-Y-encapsulated nickel phthalocyanine, 3 gm of Ni—Y was degassed for 8 h at 373 K in vacuum and then exposed to the vapors of 1,2-dicyanobenzene (10 g) at 533 K for 24 h. Nitrogen was used as a carrier gas. The solid was Soxhlet extracted with different solvents viz., acetone, pyridine, and acetonitrile. The sample NiPc-Y, thus obtained was finally dried at 373 K.

EXAMPLE 5

This example illustrates the preparation of N,N-o-phenylenebis(salicylidenaminato) copper(II) encapsulated in zeolite-Y (CuSaloph-Y). Copper exchanged Y (Cu—Y) was prepared first by ion exchanging zeolite NaY (5 g) with an aqueous solution of $Cu(NO_3)_2.2.5H_2O$ (250 mg in 100 ml distilled water). In the preparation of zeolite-Y-encapsulated CuSaloph, 3 gm of Cu—Y was degassed for 8 h at 373 K in vacuum and then exposed to the vapors of Saloph ligand (10 g) at 473 K for 24 h. Nitrogen was used as a carrier gas. The solid was Soxhlet extracted with different solvents viz., acetone, pyridine, and acetonitrile. The sample CuSaloph-Y, thus obtained was finally dried at 373 K.

EXAMPLE 6

Titanium silicalite-1 (TS-1) was prepared according to the published procedure of Thangaraj et al (J. Catal. 130, 1 (1991)). Si/Ti ratio of the catalyst is 33 and the catalyst has specific surface area of 400 $m^2/g$. The general procedure for the preparation of TS-1 is as follows: To a solution of tetraethyl orthosilictae (TEOS), in isopropyl alcohol, the appropriate amount of aqueous tetrapropyl ammonium hydroxide (20% aq. TPAOH solution) was added to partially hydrolyze the TEOS. To this resulting liquid mixture a required quantity of titanium tetrabutoxide [Ti(OBu)$_4$], in dry isopropyl alcohol was added drop wise under vigorous stirring. The clear liquid was stirred for about 1 h in order to complete the hydrolysis of TEOS and Ti(OBu)$_4$. Finally the solution of remaining TPAOH in doubled distilled water was added slowly to reaction mixture. This final mixture was stirred at 348-353 K for about 6 h to remove the alcohol. The crystallization was done at statically at 443 K for 4 days. The crystalline solid was filtered, washed dried and calcined at 823 K for 10 h.

EXAMPLE 7

This example (Run No. 1) illustrates the procedure for the preparation of cyclic carbonates from epichlorohydrin (ECH) and carbon dioxide using zeolite-based solid catalyst AlPc-Y at 393 K and 100 psig $CO_2$ pressure. The experiments were conducted in a 100 ml stainless steel pressure reactor. In a typical reaction 18 mmol ECH, 0.0072 mmol catalyst, co-catalyst N,N-dimethyl aminopyridine (0.0072 mmol) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian 3400) and identified by GC-MS (Shimadzu QP-5000), GC-IR (Perkin Elmer 2000) and $^1H$ NMR (Bruker AC 200).

EXAMPLE 8

This example (Run Nos. 2-4) illustrates the catalyst reuse experiments. The catalyst separated from the reaction mixture at the end of the experiment in EXAMPLE 6 was reused for at least 3 times adopting the same procedure and experimental conditions described in EXAMPLE 6. In the recycling experiments no loss in activity of the catalyst was observed.

EXAMPLE 9

This example (Run No. 5) illustrates the procedure for the preparation of cyclic carbonates from epichlorohydrin (ECH) and carbon dioxide using zeolite-based solid catalyst CuPc-Y at 393 K and 100 psig $CO_2$ pressure. The experiments were conducted in a 100 ml stainless steel pressure reactor. In a typical reaction 18 mmol ECH, 0.0072 mmol catalyst, co-catalyst N,N-dimethyl aminopyridine (0.0072 mmol) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian 3400) and identified by GC-MS (Shimadzu QP-5000), GC-IR (Perkin Elmer 2000) and $^1$H NMR (Bruker AC 200).

EXAMPLE 10

This example (Run No. 6) illustrates the procedure for the preparation of cyclic carbonates from epichlorohydrin (ECH) and carbon dioxide using zeolite-based solid catalyst CoPc-Y at 393 K and 100 psig $CO_2$ pressure. The experiments were conducted in a 100 ml stainless steel pressure reactor. In a typical reaction 18 mmol ECH, 0.0072 mmol catalyst, co-catalyst N,N-dimethyl aminopyridine (0.0072 mmol) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian 3400) and identified by GC-MS (Shimadzu QP-5000), GC-IR (Perkin Elmer 2000) and $^1$H NMR (Bruker AC 200).

EXAMPLE 11

This example (Run No. 7) illustrates the procedure for the preparation of cyclic carbonates from epichlorohydrin (ECH) and carbon dioxide using zeolite-based solid catalyst NiPc-Y at 393 K and 100 psig $CO_2$ pressure. The experiments were conducted in a 100 ml stainless steel pressure reactor. In a typical reaction 18 mmol ECH, 0.0072 mmol catalyst, co-catalyst N,N-dimethyl aminopyridine (0.0072 mmol) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian 3400) and identified by GC-MS (Shimadzu QP-5000), GC-IR (Perkin Elmer 2000) and $^1$H NMR (Bruker AC 200).

EXAMPLE 12

This example (Run No. 8) illustrates the procedure for the preparation of cyclic carbonates from epichlorohydrin (ECH) and carbon dioxide using zeolite-based solid catalyst CuSaloph-Y at 393 K and 100 psig $CO_2$ pressure. The experiments were conducted in a 100 ml stainless steel pressure reactor. In a typical reaction 18 mmol ECH (0.370 g), 0.015 g CuSaloph-Y, co-catalyst N,N-dimethyl aminopyridine (0.0072 mmol; 0.005 g) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian 3400) and identified by GC-MS (Shimadzu QP-5000), GC-IR (Perkin Elmer 2000) and $^1$H NMR (Bruker AC 200).

EXAMPLE 13

This example (Run No. 9) illustrates the procedure for the preparation of cyclic carbonates from epichlorohydrin (ECH) and carbon dioxide using zeolite-based solid catalyst TS-1 at 393 K and 100 psig $CO_2$ pressure. The experiments were conducted in a 100 ml stainless steel pressure reactor. In a typical reaction 18 mmol ECH, 100 mg catalyst, co-catalyst N,N-dimethyl aminopyridine (0.0072 mmol) and 20 ml $CH_2Cl_2$ were taken. The reactor was pressurized to 100 psig with $CO_2$ and the temperature was raised to 393 K and the reaction was conducted for 4 h. The reactor was then cooled to 298 K, unreacted $CO_2$ was, catalyst separated by centrifugation and the products were analyzed by GC (Varian (3400) and identified by GC-MS (Shimadzu QP-5000), GC-IR (Perkin Elmer 2000) and $^1$H NMR (Bruker AC 200).

EXAMPLE 14

This example (Run No. 10) illustrates the procedure for the preparation of cyclic carbonates from epichlorohydrin (ECH) and carbon dioxide using zeolite-based solid catalyst AlPc-Y at 393 K and 100 psig $CO_2$ pressure and using no solvent. The reaction conditions and reactants are same as that used in EXAMPLE 6 excepting that no solvent was used in the reaction.

The catalytic activity data for the preparation of cyclic carbonate from epichlorohydrin (ECH) using zeolite-based solid catalysts are listed in TABLE 1.

TABLE 1

Preparation of choloropropylene carbonate from epichlorohydrin and $CO_2$ over zeolite-based solid catalysts

| Run No. | Catalyst | Conversion (wt %) | Selectivity for cyclic carbonate (wt %) |
|---|---|---|---|
| 1 | AlPc-Y | 97.3 | 99.7 |
| 2 | AlPc-Y (recycle 1) | 95.7 | 99.3 |
| 3 | AlPc-Y (recycle 2) | 93.8 | 96.7 |
| 4 | AlPc-Y (recycle 3) | 94.0 | 98.3 |
| 5 | CuPc-Y | 91.4 | 96.3 |
| 6 | CoPc-Y | 90.9 | 95.5 |
| 7 | NiPc-Y | 83.4 | 87.7 |
| 8 | CuSaloph-Y | 64.5 | 93.8 |
| 9 | TS-1 | 92.1 | 94.2 |
| 10 | AlPc-Y (no solvent) | 93.0 | 100 |

The process described above has the combined unique advantages of high conversion of epichlorohydrin accompanied with high selectivity of cyclic carbonate. The process is environmentally friendly and does not involve toxic reactants like phosgene. Little efforts are required to separate the catalyst. The separated catalysts can be reused with no significant loss in activity.

We claim:

1. A process for preparation of cyclic carbonates comprising:
   (a) reacting an epoxide with at least carbon dioxide, in the presence of a zeolite-Y catalyst encapsulating an organometallic complex and a Lewis base co-catalyst, wherein the organometallic complex comprises a transition metal ion which is Al, Cu, Co or Ni and a coordinating ligand which is a phthalocyanine; and (b) separating the catalyst and recovering the corresponding cyclic carbonate formed.

2. A process as claimed in claim 1 wherein the reaction is carried out at a minimum pressure of 30 psig and temperature in the range of 40 to 120° C. for 0.5 to 4 hrs.

3. A process as claimed in claim 1 wherein the epoxide is of the formula $C_{(n)}H_{2(n)}O$ wherein n=2 to 10.

4. A process as claimed in claim 1 wherein the epoxide is dissolved in a solvent selected from a polar and non-polar solvent.

5. A process as claimed in claim 4 wherein the solvent is selected from the group consisting of 1,2-dichloromethane, toluene, acetonitrile, methanol and water.

6. A process as claimed in claim 1 wherein the Lewis base co-catalyst is selected from the group consisting of pyridine, a pyridine derivative, alkyl phosphine, aryl phosphine, alkyl ammonium salts and phosphonium salts.

7. A process as claimed in claim 1 wherein the carbon dioxide is provided as air or mixed with a compound selected from the group consisting of oxygen, nitrogen oxides, hydrogen peroxide and alkyl hydroperoxide.

8. A process as claimed in claim 1 wherein the ratio of the epoxide to the catalyst is in the range of 2500:1 to 5:1.

9. A process as claimed in claim 1 wherein the reaction is phosgene free.

10. A process as claimed in claim 1 wherein the catalyst is separated and recycled.

11. A process as claimed in claim 10, wherein the separation of the catalyst is carried out by filtration.

12. A process as claimed in claim 1 wherein conversion of the epoxide is greater than or equal to 85%, and selectivity for the cyclic carbonate is greater than or equal to 85%.

* * * * *